United States Patent
Randquist et al.

(10) Patent No.: US 11,534,146 B2
(45) Date of Patent: Dec. 27, 2022

(54) BIOPSY INCISION DEVICE

(71) Applicant: Dermazip AB, Saltsjöbaden (SE)

(72) Inventors: Charles Randquist, Saltsjö-Boo (SE); Henrik Falk, Stockholm (SE)

(73) Assignee: Dermazip AB, Saltsjöbaden (SE)

( * ) Notice: Subject to any disclaimer, the term of this patent is extended or adjusted under 35 U.S.C. 154(b) by 683 days.

(21) Appl. No.: 16/074,609

(22) PCT Filed: Feb. 2, 2017

(86) PCT No.: PCT/SE2017/050092
§ 371 (c)(1),
(2) Date: Aug. 1, 2018

(87) PCT Pub. No.: WO2017/135879
PCT Pub. Date: Aug. 10, 2017

(65) Prior Publication Data
US 2019/0038265 A1   Feb. 7, 2019

(30) Foreign Application Priority Data

Feb. 2, 2016 (SE) .................................. 1650125-6

(51) Int. Cl.
| | | |
|---|---|---|
| *A61B 10/02* | (2006.01) | |
| *A61B 17/3205* | (2006.01) | |
| *A61B 17/00* | (2006.01) | |
| *A61B 17/32* | (2006.01) | |
| *A61B 17/3209* | (2006.01) | |

(52) U.S. Cl.
CPC ...... *A61B 10/0266* (2013.01); *A61B 10/0233* (2013.01); *A61B 17/3205* (2013.01); *A61B 17/32093* (2013.01); *A61B 2017/00761* (2013.01); *A61B 2017/320052* (2013.01)

(58) Field of Classification Search
CPC ............ A61B 10/0266; A61B 10/0233; A61B 2017/00761; A61B 17/32093; A61B 2017/320052; A61B 17/3205
See application file for complete search history.

(56) References Cited

U.S. PATENT DOCUMENTS

| | | | |
|---|---|---|---|
| 3,902,475 A * | 9/1975 | Begg ................ | A61B 17/32093 606/182 |
| 7,591,835 B2 | 9/2009 | Warren | |
| 2004/0215217 A1 * | 10/2004 | Banbury ............ | A61B 10/0233 606/151 |
| 2007/0142853 A1 | 6/2007 | Williamson, IV et al. | |
| 2007/0232954 A1 | 10/2007 | Harris et al. | |

(Continued)

FOREIGN PATENT DOCUMENTS

GB       2073591 A       10/1981

*Primary Examiner* — Alex M Valvis
*Assistant Examiner* — Justin Xu
(74) *Attorney, Agent, or Firm* — Capitol City TechLaw

(57) ABSTRACT

A biopsy incision device (100) comprising a proximal side (101), to be arranged on a skin surface, and a distal side (102), said distal side (102) comprising a blade actuator (103) associated with at least one cutting blade (104), is provided. The blade actuator (103) and said at least one cutting blade (104) being suspended at a pivoting point (105) on said distal side (102), such that said blade actuator (103) and said at least one cutting blade (104) may pivot around a pivoting axis (A), such that said at least one cutting blade (104) may cut said skin surface.

15 Claims, 5 Drawing Sheets

(56) References Cited

U.S. PATENT DOCUMENTS

| | | |
|---|---|---|
| 2009/0018467 A1 | 1/2009 | Chiu et al. |
| 2012/0109172 A1* | 5/2012 | Schmitz ................ A61M 1/79 606/170 |
| 2012/0283793 A1* | 11/2012 | Burroughs, III ... A61B 17/3205 606/86 R |
| 2014/0073987 A1 | 3/2014 | Kang et al. |

* cited by examiner

BIOPSY INCISION DEVICE

This application claims priority under 35 USC 119(a)-(d) to SE patent application No. 1650125-6, which was filed on Feb. 2, 2016, the entire contents of which are incorporated herein by reference.

FIELD OF THE INVENTION

This invention pertains in general to medical devices. More particularly, the present invention relates to a biopsy incision device.

BACKGROUND OF THE INVENTION

A biopsy or excision typically removes a section of tissue, usually containing the full dermis and in some cases the subcutaneous fatty layer as well. Such excisions typically leave an opening in the skin that requires closing. Such excision openings are ideally elliptical, for facilitating bringing the skin edges together. Not only that, but the cut preferably has a depth pattern that corresponds to the cut width, i.e. a smaller depth at a smaller width and vice versa. However, this is difficult to achieve if the incision is performed freehand. Typically a biopsy incision is performed via a freehand technique where the surgeon uses a scalpel to cut an elliptical or spherical mass of tissue from the skin surface of a patient. As the surgeon guides the scalpel with their hands they determine the form of the incision leading to an incision that could be any number of shapes or sizes. This in turn leads to less reliable healing of the incision wound, and different surgeons have differing competences with respect to performing skin surface biopsies.

U.S. Pat. No. 7,591,835 discloses a skin cutting device, wherein a knife may follow knife guides along the periphery of a cutting area. Even if these knife guides allow for an improved one two dimensional cutting line, a biopsy can not be removed without cutting also along the skin plane. Still further, the knife is only guided in a way assuring correct lateral position at a constant height, but the central position can not be assured and it does not allow for a controlled way of adapting depth to width.

SUMMARY OF INVENTION

Accordingly, the present invention preferably seeks to mitigate, alleviate or eliminate one or more of the above-identified deficiencies in the art and disadvantages singly or in any combination and solves at least the above mentioned problems by providing a biopsy incision device comprising: a proximal side to be arranged on a skin surface of a patient, and a distal side comprising a blade actuator associated with at least one cutting blade. The blade actuator and the at least one cutting blade are suspended at a pivoting point on the distal side, such that said blade actuator and the at least one cutting blade may pivot around a pivoting axis, such that the at least one cutting blade may cut said skin surface.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description of the present invention describes a biopsy incision device.

Figure 1:
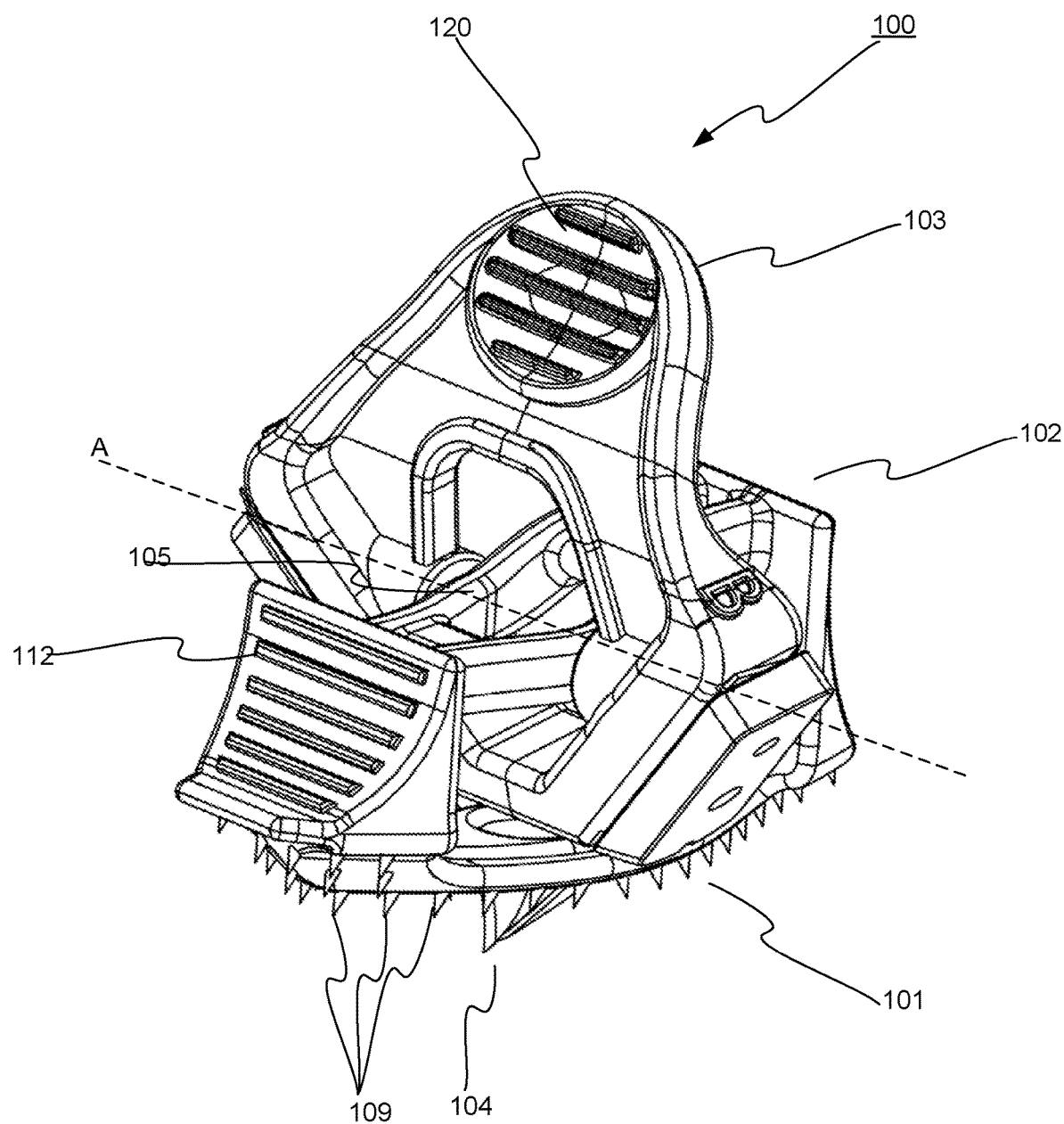
FIG. 1 is a perspective view of the biopsy incision device.

FIG. 1 illustrates a biopsy incision device 100 comprising a proximal side 101 which may be arranged on a skin surface. The biopsy incision device 100 further comprises a distal side 102. The distal side comprises a blade actuator 103 associated with at least one cutting blade 104.

The blade actuator 103 and the at least one cutting blade 104 are suspended at a pivoting point 105 on said distal side 102, such that said blade actuator 103 and said at least one cutting blade 104 may pivot around a pivoting axis A, such that said at least one cutting blade 104 may cut said skin surface. The pivoting axis A is generally parallel to the skin surface at the proximal side 101. The blade actuator 103 can actuate the at least one cutting blade 104 through an arc on a skin surface at the proximal side 101. The blade actuator 103 associated with the at least one cutting blade 104 allows the biopsy incision device 100 to create an incision at a skin surface having a reliable and consistent form.

During use the proximal side 101 may be arranged on a skin surface. The distal side 102 is in such an arrangement distal from the skin surface.

Figure 5:
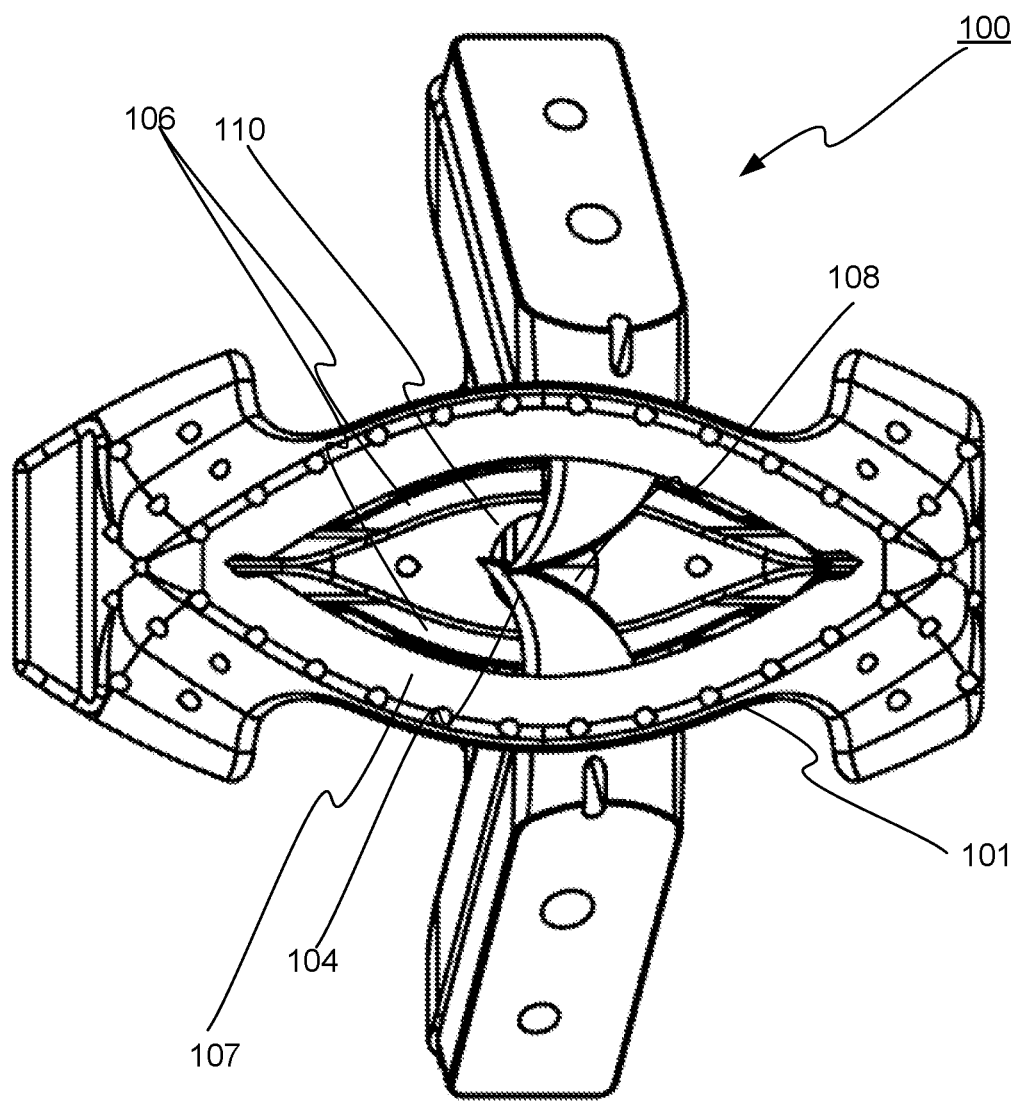
FIG. 5 is a perspective view directed towards the proximal side of the biopsy incision device.

As can be seen in FIG. 5 the proximal side 101 comprises a centre plate 110. Circumferentially of the centre plate 110 cutting tracks/blade guides 106 may be arranged. Laterally of the cutting tracks/blade guides 106 an outer support region 107 may be arranged.

The centre plate 110 may be eye-shaped or elliptical. The lateral edges of the centre plate 110 are formed by the cutting tracks/blade guides 106, such that cutting tracks/blade guides 106 forms a eye-shape or elliptical shape. In this way the incision/cut may be eye-shaped or elliptically shaped, which is preferred for facilitated subsequent closure of the cut/incision.

As shown in FIG. 5 the centre plate 110 can be provided with cutting tracks/blade guides 106, such that the at least one cutting blade 104 is guided and laterally supported during blade actuation. The guides 106 can be opposing arc formed cut-outs such that the at least one cutting blade 104 is guided through an elliptical or eye-shaped path. The guides 106 may be angled in relation to the skin surface or the proximal side 101, such that the guides 106 may guide the at least one cutting blade 104 in an angle α being selected to be in the interval from 15 to 75 degrees. The blade guides can further improve the reliability of the cut. The centre plate 110 forms the medial edge of the blade guides 106. The outer support region 107 forms the lateral edge of the blade guides 106.

Grip flanges 111, 112 can extend distally from the outer support region 107 on the proximal side 101 and at ends of the incision device 100, corresponding to the edges of the eye-shaped/elliptical centre plate 110. Hence, the grip flanges 111,112 can extend distally at the ends of the biopsy incision device 100. The grip flanges 111,112 can also connect the proximal side 101 of the biopsy incision device 100 to the distal side 102.

The grip flanges 111, 112 can extend from positions other than the ends of the device 100. However, by extending from the ends the medial area of the biopsy incision device 100 can be substantially free from obstructions allowing better sight of the incision zone. The grip flanges 111, 112 allow the device 100 to be more easily held in place during operation. The device may be provided with, as is shown in FIGS. 1-5 a pair of opposing grip flanges 111, 112 at each end of the device. The pair of grip flanges 111, 112 may form a grippable surface.

Figure 2:
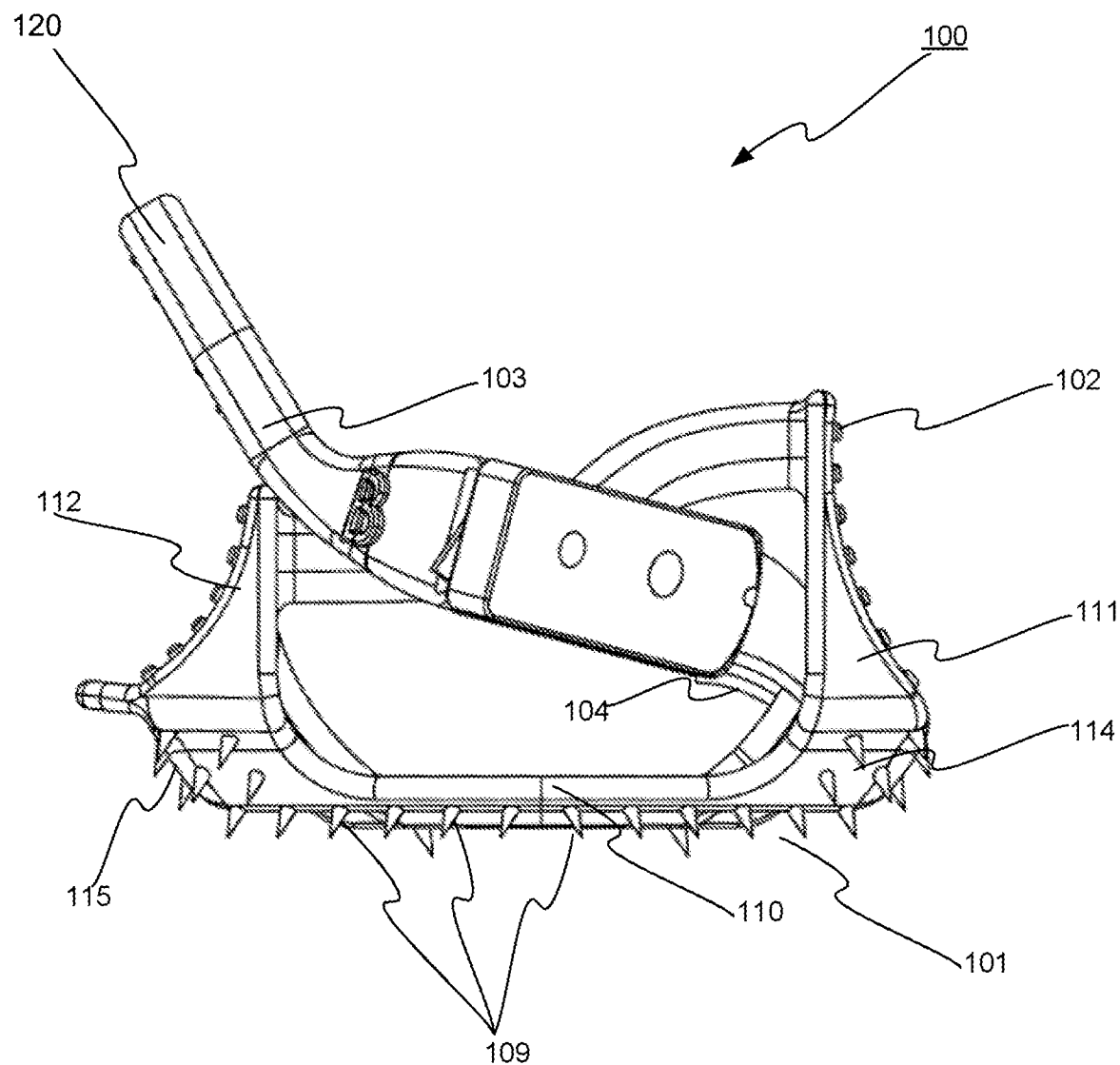
FIG. 2 is a side perspective view of the biopsy incision device.
Figure 3:
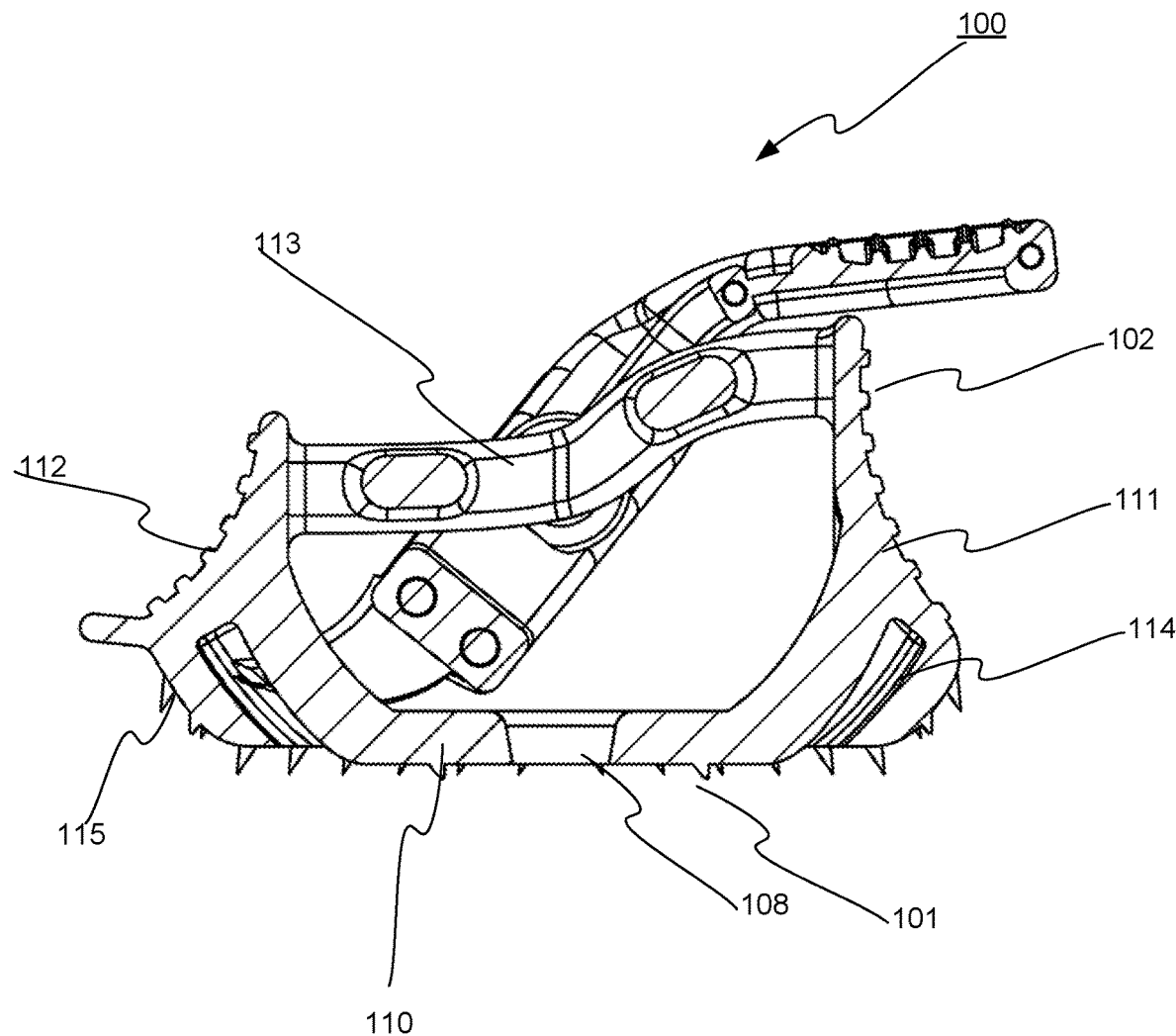
FIG. 3 is a cross-sectional side view of the biopsy incision device.

The proximal side 101 of the biopsy incision device 100 can be substantially planar, such that the proximal side 101 is ideal for placing against a flat skin surface. In FIGS. 2 and 3 distally extending curved regions 114, 115 connecting the outer region 107 on the proximal side 101 to the grip flanges 111, 112 are shown. These curved regions 114,115 may not be necessary and ideally the proximal side 101 is substantially flat. In such a design the centre plate 110 is planar with the proximal ends of the grip flanges 111, 112.

The centre plate 110 can further be provided with an aperture 108. The aperture 108 allows visual positioning of the biopsy incision device 100 over an incision zone. The aperture 108 can be circular, elliptical or any other shape which enables visual access to the skin under the biopsy incision device 100.

The proximal surface of the center plate 110 can be provided with a means for maintaining the biopsy incision device 100 in position at the skin surface during incision. In this case the proximal surface is intended to mean the face of the proximal side which sits nearest the skin surface. The means for maintaining the position can be, as shown in FIGS. 1 to 5, a plurality of spikes 109, such that the biopsy incision device 100 can be held in place against the skin surface. The spikes 109 pierce or partially pierce the skin surface to maintain the position of the biopsy incision device 100. The spikes may also simply be considered to grip the skin surface. The spikes mean that the operator does not need to apply any substantial lateral forces to the biopsy device during operation to hold it in place.

The distal side 102 of the biopsy incision device may be provided with a cross member 113. The cross member 113 may be provided with a hinge region forming the pivot point 105. The cross member 113 may furthermore be provided with at least one aperture (seen in FIG. 1), such that the aperture 108 in the center plate 110, and the aperture in the cross member 113 form an area providing visual access to the incision zone when in use. The cross member 113 may be formed by at least one beam, for example, two parallel beams, extending between the grip flanges 111, 112. The beams may be provided with at least one pin to form the pivot point 105 for the blade actuator 103 described above.

The at least one cutting blade 104 can have a pre-cut hidden position, wherein said at least one cutting blade 104 is positioned distally of said proximal side 101. The at least one cutting blade 104 can also have a post-cut hidden position, preferably together with the pre-cut hidden position, wherein said at least one cutting blade 104 is positioned distally of said proximal side 101. The at least one cutting blade 104 can further have an exposed position wherein at least a portion of said at least one cutting blade 104 is positioned proximally of said proximal side 101. In the hidden positions the at least one cutting blade cannot contact the skin surface. In the exposed position the at least one cutting blade can contact the skin surface. The hidden positions can be a storage or non-activated position. The cutting blade 104 and/or blade actuator 103 may be lockable in the hidden positions. The locking function may be achieved by retentive friction between the blade actuator and/or the at least one cutting blade 104.

The at least one cutting blade 104 is generally a thin, flat blade having a single cutting edge. The at least one cutting blade 104 may be provided with a bevelled edge. The bevelled edge reduces the force required to pierce the skin surface. The at least one cutting blade may be scalpel like with a single bevelled edge. The at least one cutting blade may also be provided with opposing bevelled edges such that two opposing cutting surfaces are created.

The at least one cutting blade 104 may be arranged as shown in FIGS. 1 to 5 in a V-shape, having a vertex positioned at the proximal side 101 of the biopsy incision device 100. The at least one cutting blade may be formed by a monolithic cutting blade. The at least one cutting blade may also be formed two cutting blades, arranged such that their proximal edges substantially meet as shown in FIG. 5. The at least one cutting blade may also be corrugated. A corrugated cutting blade may increase skin penetration in some instances.

Figure 4:
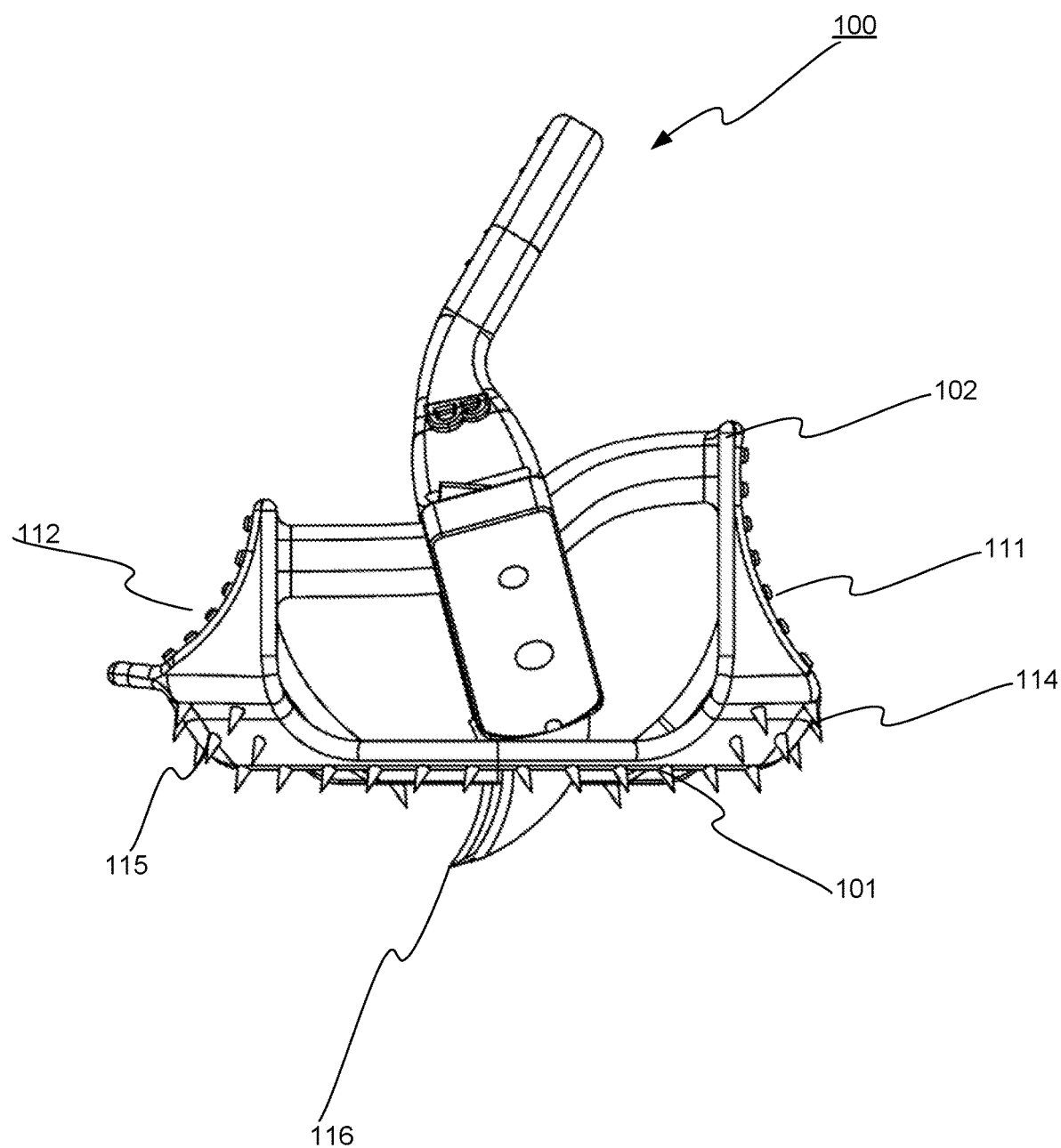
FIG. 4 is a side perspective view of the biopsy incision device showing the at least one cutting blade.

As shown in FIGS. 4 and 5 the at least one cutting blade 104 may be provided with a point 116 extending at an angle from the axis of extension of the blade such that the point initially pierces the skin surface during blade actuation. As shown in FIGS. 4 and 5 the point 116 may be provided such that the tip of the at least one cutting blade is curved.

The at least one cutting blade 104 is generally constructed from a metal such as stainless steel or carbon steel. However, the at least one cutting blade could be constructed from any rigid material that is suitable for incision in the skin surface, for example, titanium or ceramics.

The blade actuator 103 extends distally from the proximal side of the biopsy incision device 100. The blade actuator 103 is associated with the at least one cutting blade 104. The at least one cutting blade 104 can be fixable to the blade actuator 103. The at least one cutting blade 104 can be fixed via a clamping member which applies a force on the at least one cutting blade 104 such that it is held to the blade actuator 103. The blade actuator 103 can further be provided with members such as pins or screws such that the at least one cutting blade is held in place. The blade actuator extends distally from the proximal side of the biopsy incision device 100. The blade actuator 103 can be associated with the distal side of the biopsy incision device 100 at a pivoting point 105. The blade actuator 103 and the at least one cutting blade 104 can be suspended from the pivoting point such that blade actuator and the at least one cutting blade 104 may pivot around a pivoting axis A which is formed at the pivot point 105. The blade actuator can extend distally beyond the pivoting point such that a region distal to the pivot point is formed. As shown in FIGS. 1-5 the blade actuator 103 can extend such that a grippable tab 120 is formed.

During operation, that is when performing an incision the biopsy incision device 100 is placed with the proximal side 101 at the skin surface of a patient on whom an excision or biopsy is to be performed. The at least one cutting blade 104 may be in a pre-cut and post-cut hidden position or non activated position. The spikes 109 provided on the proximal surface of the centre plate 110 grip the skin surface. The operator may hold the grip flanges 111, 112 to position the biopsy incision device laterally and apply a force toward the skin surface.

An operator can grip the blade actuator 103 at, for example, the grippable tab 120. The operator can then pivot the blade actuator 103 around the pivot point 105. In doing so the blade actuator moves the at least one cutting blade 104 such that it contacts the skin surface. Further force on the blade actuator 103 can cause the at least one cutting blade 104 to pierce the skin surface. As the blade actuator 103 is moved further the at least one cutting blade 104 makes an incision in the skin surface. The excision formed by the device is an eye-shaped or elliptical wedge having an apex edge being an arc.

Although, the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A biopsy incision device comprising:
    a proximal side to be arranged on a skin surface; and
    a distal side that includes a blade actuator supporting at least two cutting blades;
    wherein the blade actuator and the at least two cutting blades are suspended at a pivot point on the distal side, such that the blade actuator and the at least two cutting blades are pivotable around a pivot axis, whereby the at least two cutting blades may cut the skin surface;
    wherein the at least two cutting blades are arranged such that proximal edges of the at least two cutting blades substantially meet; and
    wherein the at least two cutting blades are configured with a curvature.

2. The biopsy incision device according to claim 1, wherein the at least two cutting blades have a pre-cut hidden position or a post-cut hidden position, in which the at least two cutting blades are positioned distally of the proximal side; and
    wherein the at least two cutting blades have an exposed position, in which the at least two cutting blades are positioned proximally of the proximal side.

3. The biopsy incision device according to claim 1, wherein the blade actuator is adapted to actuate the at least two cutting blades through an arc on a skin surface at the proximal side.

4. The biopsy incision device according to claim 1, wherein the pivot axis is parallel to the skin surface at the proximal side.

5. The biopsy incision device according to claim 1, further comprising a center plate arranged at the proximal side;
    wherein the center plate includes an aperture allowing visual positioning of the biopsy incision device over an incision zone.

6. The biopsy incision device according to claim 5, wherein a proximal surface of the center plate is provided with a plurality of spikes, such that the biopsy incision device can be held in place against the skin surface.

7. The biopsy incision device according to claim 1, wherein a proximal surface of the proximal side is provided with a plurality of spikes, such that the biopsy incision device can be held in place against the skin surface.

8. The biopsy incision device according to claim 1, wherein each of the at least two cutting blades has a bevelled edge.

9. The biopsy incision device according to claim 1, wherein each of the at least two cutting blades has a V-shape, with a vertex positioned at the proximal side of the biopsy incision device.

10. The biopsy incision device according to claim 1, wherein the at least two cutting blades and/or the blade actuator is lockable, such that the at least two cutting blades do not extend proximally beyond the proximal side.

11. The biopsy incision device according to claim 1, wherein the blade actuator extends distally from the proximal side of the biopsy incision device forming a grippable tab.

12. The biopsy incision device according to claim 1, further comprising grip flanges extending distally from ends of the biopsy incision device.

13. The biopsy incision device according to claim 12, further comprising a center plate arranged at the proximal side;
    wherein the center plate is planar with proximal ends of the grip flanges.

14. The biopsy incision device according to claim 1, further comprising a pair of opposed grip flanges extending distally from ends of the biopsy incision device such that the pair of grip flanges forms a grippable surface.

15. The biopsy incision device according to claim 1, wherein each of the at least two cutting blades is provided with a point extending at an angle from an axis of extension of the respective cutting blade such that the point initially pierces the skin surface during blade actuation.

* * * * *